(12) United States Patent
Arnone et al.

(10) Patent No.: US 7,904,308 B2
(45) Date of Patent: Mar. 8, 2011

(54) METHOD AND SYSTEM FOR PROVIDING INDEXING AND CATALOGUING OF ORTHODONTIC RELATED TREATMENT PROFILES AND OPTIONS

(75) Inventors: Robert Arnone, Pleasanton, CA (US); Eric Kuo, Foster City, CA (US); Doug Bukaty, Lake Forest, IL (US)

(73) Assignee: Align Technology, Inc., San Jose, CA (US)

( * ) Notice: Subject to any disclaimer, the term of this patent is extended or adjusted under 35 U.S.C. 154(b) by 1359 days.

(21) Appl. No.: 11/379,198

(22) Filed: Apr. 18, 2006

(65) Prior Publication Data

US 2007/0244718 A1    Oct. 18, 2007

(51) Int. Cl.
*G06Q 10/00* (2006.01)
*G06Q 50/00* (2006.01)
*A61B 5/00* (2006.01)
*G06F 19/00* (2006.01)
*A61C 3/00* (2006.01)

(52) U.S. Cl. ................... 705/2; 705/3; 433/24
(58) Field of Classification Search ............. 705/2–4
See application file for complete search history.

(56) References Cited

U.S. PATENT DOCUMENTS

| | | | | |
|---|---|---|---|---|
| 7,134,874 B2 * | 11/2006 | Chishti et al. | ................ | 433/24 |
| 7,140,877 B2 * | 11/2006 | Kaza | ................ | 433/24 |
| 7,220,122 B2 * | 5/2007 | Chishti | ................ | 433/24 |
| 2002/0010568 A1 * | 1/2002 | Rubbert et al. | ................ | 703/6 |
| 2002/0025503 A1 | 2/2002 | Chapoulaud et al. | | |
| 2002/0064752 A1 | 5/2002 | Durbin et al. | | |
| 2003/0021453 A1 * | 1/2003 | Weise et al. | ................ | 382/128 |
| 2003/0064345 A1 * | 4/2003 | Chishti et al. | ................ | 433/24 |
| 2003/0215764 A1 | 11/2003 | Kopelman et al. | | |
| 2004/0029068 A1 * | 2/2004 | Sachdeva et al. | ................ | 433/24 |
| 2004/0197728 A1 * | 10/2004 | Abolfathi et al. | ................ | 433/24 |
| 2004/0214128 A1 | 10/2004 | Sachdeva et al. | | |
| 2004/0259049 A1 | 12/2004 | Kopelman et al. | | |
| 2005/0186526 A1 * | 8/2005 | Stewart et al. | ................ | 433/24 |
| 2005/0271996 A1 | 12/2005 | Sporbert et al. | | |

(Continued)

FOREIGN PATENT DOCUMENTS

WO    WO-01/80763    11/2001

(Continued)

OTHER PUBLICATIONS

International Search Report and Written Opinion of the International Searching Authority for International Application No. PCT/US2007/066809 filed Apr. 17, 2007 to Align Technology, Inc.

(Continued)

*Primary Examiner* — Neal R Sereboff
(74) *Attorney, Agent, or Firm* — Brooks, Cameron & Huebsch, PLLC

(57) ABSTRACT

Method and system for providing an orthodontic profile indexing and treatment plan including comparing an initial patient condition in each of a plurality of dentition categories with one or more reference conditions in each of the plurality of dentition categories, wherein each of the one or more reference conditions has a corresponding representation, selecting at least one reference condition in one or more of the plurality of dentition categories, where each selected reference condition is similar to the initial patient condition in a same dentition category, and generating a patient identifier based on the corresponding representations of each selected reference condition is provided.

13 Claims, 11 Drawing Sheets

| Category 201 | Component 202 | #1 203 | #2 203 | #3 203 | #4 203 | #5 203 | #6 203 | #7 203 | Number of Options 204 |
|---|---|---|---|---|---|---|---|---|---|
| Sagittal | Right Canine | Right Canine Full Class 2+ | Right Canine Full Class 2 | Right Canine Partial Class 2 | Right Canine Class 1 | Right Canine Partial Class 3 | Right Canine Full Class 3 | Right Canine Full Class 3+ | 7 |
| Vertical | Anterior Overbite | Severe Anterior Deep Bite | Moderate Anterior Deep Bite | Mild Anterior Deep Bite | Normal Anterior Overbite | Mild Anterior Open Bite | Moderate Anterior Open Bite | Severe Anterior Open Bite | 7 |
| Horizontal | Upper Midline Relative to Lower Midline | Upper Midline to Right 2+ mm | Upper Midline to Right 1-2 mm | Upper Midline to Right 0-1 mm | Upper Midline Centered | Upper Midline to Left 0-1 mm | Upper Midline to Left 1-2 mm | Upper Midline to Left 2+ mm | 7 |
| Arch Length | Lower Arch Length | Lower Severe Crowding | Lower Moderate Crowding | Lower Mild Crowding | No Lower Discrepancy | Lower Mild Spacing | Lower Moderate Spacing | Lower Severe Spacing | 7 |

200

U.S. PATENT DOCUMENTS

2006/0057533 A1 3/2006 McGann
2006/0078842 A1 4/2006 Sachdeva et al.

FOREIGN PATENT DOCUMENTS

WO    WO-2006/100700     9/2006

OTHER PUBLICATIONS

International Preliminary Report on Patentability and Written Opinion of the International Searching Authority for PCT Application No. PCT/US2007/066809 filed Apr. 17, 2007, mailed Oct. 30, 2008.

* cited by examiner

| Category 201 | Component 202 | #1 203 | #2 203 | #3 203 | #4 203 | #5 203 | #6 203 | #7 203 | Number of Options 204 |
|---|---|---|---|---|---|---|---|---|---|
| Sagittal | Right Canine | Right Canine Full Class 2+ | Right Canine Full Class 2 | Right Canine Partial Class 2 | Right Canine Class 1 | Right Canine Partial Class 3 | Right Canine Full Class 3 | Right Canine Full Class 3+ | 7 |
| Vertical | Anterior Overbite | Severe Anterior Deep Bite | Moderate Anterior Deep Bite | Mild Anterior Deep Bite | Normal Anterior Overbite | Mild Anterior Open Bite | Moderate Anterior Open Bite | Severe Anterior Open Bite | 7 |
| Horizontal | Upper Midline Relative to Lower Midline | Upper Midline to Right 2+ mm | Upper Midline to Right 1-2 mm | Upper Midline to Right 0-1 mm | Upper Midline Centered | Upper Midline to Left 0-1 mm | Upper Midline to Left 1-2 mm | Upper Midline to Left 2+ mm | 7 |
| Arch Length | Lower Arch Length | Lower Severe Crowding | Lower Moderate Crowding | Lower Mild Crowding | No Lower Discrepancy | Lower Mild Spacing | Lower Moderate Spacing | Lower Severe Spacing | 7 |

| | | Goal |
|---|---|---|
| Treatment Goal | 1 | Align for Restorative Dentistry |
| | 2 | Esthetic Alignment |
| | 3 | Align to Class 1 Canine |
| | 4 | Align to Ideal |

FIGURE 3

| | Treatment Goal | GOAL | ADDRESS |
|---|---|---|---|
| 1 | | Align for Restorative Dentistry | XXX4 |
| 2 | | Esthetic Alignment | XX44 |
| 3 | | Align to Class 1 Canine | 4X44 |
| 4 | | Align to Ideal | 4444 |

| Date | 12/15/2005 | | |
|---|---|---|---|
| Doctor Name | Dr. John Jones | | |
| Patient Name 601 | Ron Smith | | |
| Gender 602 | Male | | |
| Chief Concern(s) 603 | Upper Spaces | Upper Crowding | High Canines |
| | Lower Spaces | Lower Crowding | Crossbite |
| | Buck Teeth | Open Bite | Bad Back Bite |

| Summary | Component | | |
|---|---|---|---|
| Sagittal | Right Canine | Right Canine Partial Class 2 | EDIT |
| Vertical | Anterior Overbite | Moderate Anterior Deep Bite | EDIT |
| Horizontal | Upper Midline Relative to Lower Midline | Upper Midline to Left 0-1 mm | EDIT |
| Arch Length | Lower Arch Length | Lower Moderate Crowding | EDIT |
| | | | |
| | | | |

| Patient | Database Address | Sagital | Vertical | Horizontal | Upper Arch Length | Lower Arch Length | Rotation | Vertical Correct | Midline Correct |
|---|---|---|---|---|---|---|---|---|---|
| M. Jones | 97557557 | Class II | Deep Bite | No Cross bite | Normal Spacing | Moderate Crowding | No Rotation | No Intrusion/ Extraction | < 2MM Midline Correct |
| Treat? | | Y/N | Y/N | | | Y/N | | | Y/N |
| L. Smith | 55772752 | Class I | Normal | Cross Bite | Moderate Crowding | Moderate Spacing | < 20° Rotation | No Intrusion/ Extraction | > 2 MM Midline Correct |
| Treat? | | | | Y/N | Y/N | Y/N | Y/N | | Y/N |

| | Dimension | Component | 1 | 2 | 3 | 4 | 5 | 6 | 7 | SELECTED VALUE |
|---|---|---|---|---|---|---|---|---|---|---|
| A | Sagittal | Right Canine | Right Canine Full Class 2+ | Right Canine Full Class 2 | Right Canine Partial Class 2 | Right Canine Class 1 | Right Canine Partial Class 3 | Right Canine Full Class 3 | Right Canine Full Class 3+ | 3 |
| B | Vertical | Anterior Overbite | Severe Anterior Deep Bite | Moderate Anterior Deep Bite | Mild Anterior Deep Bite | Normal Anterior Overbite | Mild Anterior Open Bite | Moderate Anterior Open Bite | Severe Anterior Open Bite | 2 |
| C | Horizontal | Upper Midline Relative to Lower Midline | Upper Midline to Right 2+ mm | Upper Midline to Right 1-2 mm | Upper Midline to Right 0-1 mm | Upper Midline Centered | Upper Midline to Left 0-1 mm | Upper Midline to Left 1-2 mm | Upper Midline to Left 2+ mm | 5 |
| D | Arch Length | Lower Arch Length | Lower Severe Spacing | Lower Moderate Spacing | Lower Mild Spacing | No Lower Discrepancy | Lower Mild Crowding | Lower Moderate Crowding | Lower Severe Crowding | 6 |

FIGURE 15

| | GOAL ADDRESS (Condensed - FIG.3) | GOAL ADDRESS (Expanded - FIG. 4) | COMBINED ADDRESS (Condensed) | COMBINED ADDRESS (Expanded) |
|---|---|---|---|---|
| INITIAL ADDRESS | | | | |
| 3256 | 1 | 3254 | 3256:1 | 3245:3254 |
| 3256 | 2 | 3244 | 3256:2 | 3256:3244 |
| 3256 | 3 | 4244 | 3256:3 | 3256:4244 |
| 3256 | 4 | 4444 | 3256:4 | 3256:4444 |

FIGURE 16

| SAMPLE DATABASE | | DATABASE ADDRESS | | | |
| --- | --- | --- | --- | --- | --- |
| | | 3256:1 | 3256:2 | 3256:3 | 3256:4 |
| | Text Description | Align for lower anterior veneers | Aligner lower anteriors and center midlines | Achieve class I canine, align lowers and center midlines | Achieve class I canine, ideal overbite, ideal alignment and center midlines |
| | Treatment Length | <6 months | 6-12 months | 12-16 months | 24+ months |
| | Skill Set 1 - restorative dentistry | Yes | Maybe | Maybe | Maybe |
| | Skill Set 2 - Orthodontic Auxiliaries | No | No | Maybe | Maybe |
| | Skill Set 3 - Sectional fixed appliances | No | No | Maybe | Yes |
| | Sample Case | Case #1425 | Case #2634 | Case #3324 | Case #5243 |
| | Case Difficulty | Easy | Easy | Moderate | Difficult |

FIGURE 17

METHOD AND SYSTEM FOR PROVIDING INDEXING AND CATALOGUING OF ORTHODONTIC RELATED TREATMENT PROFILES AND OPTIONS

FIELD OF THE INVENTION

The present invention is related generally to the field of orthodontics. More specifically, the present invention is related to methods and system for providing indexing orthodontic related treatment profiles and options.

BACKGROUND

A primary objective of orthodontics is to realign patients' teeth to positions where the teeth function optimally and have an aesthetic appearance. The goal of a doctor is to take the patient from their current condition ("initial" or "starting dentition") to a final condition ("treatment goal"). The result achieved is known as the "treatment outcome." There may be many ways to achieve the goal and these are known as "treatment options." The methodologies used by the doctor to get the patient to the goal are the known as the "treatment plan."

Often times, doctors establish the goal as "ideal" and discontinue treatment when they are as close as they can possibly get to the ideal. However, more recently with the growing use of 3-D computer graphics software services and programs in dentistry, the doctor can actually establish a custom treatment goal specific to each individual patient, and this goal may be a limited treatment goal and not ideal in every component of the bite. This is important because if the doctor is able to achieve 100% of the intended limited goal, the treatment may still be deemed a success, whereas it may be possible that if the doctor only achieves 75% of a completely "ideal" treatment goal, the treatment might not be deemed a success even though the amount of measured improvement on an absolute scale in the latter situation might be higher than in the limited treatment situation.

Typically, appliances such as fixed braces and wires are applied to a patient's teeth to gradually reposition them from an initial arrangement to a final arrangement. The diagnosis and treatment planning process of orthodontic cases can be imprecise as the final dentition of a patient is based on the knowledge and expertise of the treating doctor in assembling various parameters in an assessment of each patient's condition and in a determination of a final position for each tooth. Different clinicians will vary in their definitions of individual orthodontic parameters and their definition of how a case should ideally be treated will also often vary.

To overcome some of these subjective issues, various indices have been used to more objectively define a patient's initial dentition and final outcome. For example, the PAR (Peer Assessment Rating) index identifies how far a tooth is from a good occlusion. A score is assigned to various occlusal traits which make up a malocclusion. The individual scores are summed to obtain an overall total, representing the degree a case deviates from ideal functional alignment and occlusion. The PAR grader is then calibrated to a known standard set of orthodontic conditions so this individual is able to rate new cases similarly.

In PAR, a score of zero would indicate ideal alignment and positioning of all orthodontic dental components as defined by generally accepted occlusal and aesthetic relationships the orthodontic community has adopted, and higher scores would indicate increased levels of irregularity. The overall score can be recorded on both pre- and post-treatment dental casts. The difference between these scores represents the degree of improvement as a result of orthodontic intervention. In addition to the PAR index, other indices may be used such as ICON, IOTN and ABO. These indices also rely on individual dental measurements in order to derive an assessment of deviation from an ideal.

What is missing from the current indices is a system for case classification categorization. While there may exist classification systems for individual components of a dental malocclusion, a systematic method to objectively classify and catalogue the entire orthodontic dental condition in each dimension does not exist. More importantly, because in the majority of orthodontic treatment, a patient-specific treatment goal is not pre-established (other than "ideal") and used as a basis from which to judge the achieved treatment outcome, not only does a need exist to define parameters in such a way that each dental parameter of a patient's individual dentition can be objectively labeled, catalogued, and searched, there also exists a need to create an indexing system that can also be used to objectively characterize a patient's treatment goal in addition to the starting dentition, treatment outcome and treatment plan, so that specific guidance can be provided on future treatment plans, and also so that meta-analyses can be conducted to better understand the broader patient population.

In view of the foregoing, it would be desirable to have methods and systems to provide indexing and cataloguing of orthodontic related diagnostic and treatment components.

SUMMARY OF THE INVENTION

In view of the foregoing, in accordance with the various embodiments of the present invention, there are provided methods and system for objectively cataloguing orthodontic profiles and associating the profiles to a patient's starting dentition, target dentition, final dentition, treatment options and treatment plan.

These and other features and advantages of the present invention will be understood upon consideration of the following detailed description of the invention and the accompanying drawings.

BRIEF DESCRIPTION OF THE DRAWINGS

FIG. 2 illustrates a tabular representation of the indexing system stored in the storage unit of FIG. 1 in accordance with one embodiment of the present invention;

FIG. 3 illustrates a representation of possible treatment goals for any given orthodontic case in one aspect of the present invention;

FIG. 6 illustrates the selection process display for use in the indexing system for the identified primary concern as "buck teeth" in accordance with one embodiment of the present invention;

FIG. 13 illustrates an exemplary patient summary display 1300 displayed on terminal 101 for use in the indexing system in accordance with one embodiment of the present invention;

FIG. 14 illustrates a patient database 1400 in accordance with one embodiment of the present invention;

FIG. 15 illustrates the selection process for representative components for use in the indexing system in accordance with an embodiment of the present invention;

FIG. 16 illustrates an exemplary series of database addresses generated by combining the initial condition address with the treatment goal address in one embodiment of the present invention;

FIG. 17 illustrates an exemplary database for a patient in another embodiment of the present invention.

DETAILED DESCRIPTION

Figure 1:
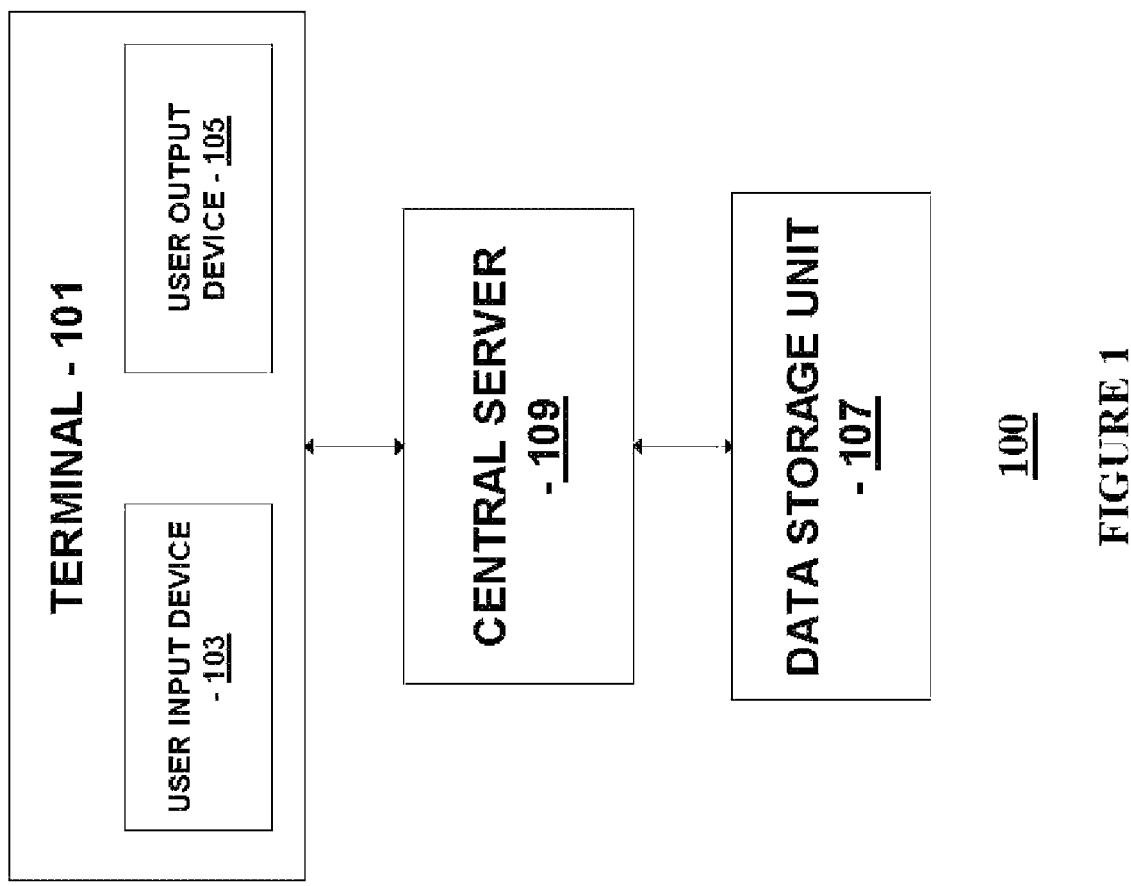
FIG. 1 is a block diagram of the overall system for practicing the various embodiments of the present invention.

FIG. 1 is a block diagram of the overall indexing system 100 for practicing the various embodiments of the present invention. The indexing system 100 in one embodiment includes a terminal 101, which may be configured as a personal computer, workstation, or mainframe, and which includes a user interface input device 103 and a user interface output device 105, a storage unit 107, and a central server 109.

Referring to FIG. 1, the user interface input device 103 may include a keyboard and may further include a pointing devices and/or a scanner, including x-ray or intra-oral scanner. The pointing device may be an indirect pointing device such as a mouse, trackball, touchpad, or graphics tablet, or a direct pointing device such as a touchscreen incorporated into the user interface output device 150. Other types of user interface input devices, such as voice recognition systems, may be used within the scope of the present invention.

Referring again to FIG. 1, the user interface output device 105 may include a printer and a display subsystem, which includes a display controller and a display device coupled to the controller. The display device may be a cathode ray tube (CRT), a flat-panel device such as a liquid crystal display, or a projection device. The display subsystem may also provide nonvisual display such as audio output.

The indexing system 100 shown in FIG. 1 also includes the data storage unit 107 which is configured to, under the access and control of either a central server 109 or a client application, to maintain the basic programming and data constructs that provide the functionality of the present invention. Software is stored in storage unit 107 which may include a memory unit and file storage unit. The memory unit may include a main random access memory (RAM) for storage of instructions and data during program execution and a read-only memory (ROM) in which fixed instructions are stored.

The file storage unit of the data storage unit 107 may provide persistent (nonvolatile) storage for program and data files, and typically includes at least one hard disk drive and at least one CD-ROM drive (with associated removable media). There may also be other devices such as a floppy disk drive and optical drives (all with their associated removable media). Additionally, the file storage unit 113 may include drives of the type with removable media cartridges, such as hard disk cartridges and flexible disk cartridges. One or more of the drives may be located at a remote location, such as in central server 109 on a local area network or at a site on the Internet's World Wide Web or the entire system may be a stand-alone software application resident on the user's system.

In one aspect of the present invention, the central server 109 may be configured to communicate with the terminal 101 and storage unit 107 to access software stored in the storage unit 107 based on and in response to the input received from terminal 101, and to perform additional processing based on procedures and/or routines in accordance with the instructions or input information received from the terminal 101.

Referring back to FIG. 1, the indexing system 100 in accordance with one embodiment of the present invention organizes orthodontic needs by the most common configurations of orthodontic discrepancies in the different dimensions: sagittal, vertical, horizontal/transverse, and arch length. The categories may be expanded to specifically capture other components such as facial profile, individual dental configurations, dynamic functional relationships, and surrounding soft tissue conditions; however discrepancies in these four categories capture a significant portion of orthodontic related dental problems or concerns. Within each category, there may be a predetermined number of individual components to characterize the potential conditions for that dimension. For each condition, a predetermined combination of different possible conditions may be created. This collection of predefined combinations for each component, where each component belongs to one of the four main categories described, in one embodiment defines a matrix such that any patient at any time point may be defined as a specific address within the matrix. Both the matrix and address matrix may be stored in storage unit 107.

FIG. 2 illustrates an exemplary tabular representation of the indexing system matrix stored in the storage unit 107 of FIG. 1 in accordance with one embodiment of the present invention. The exemplary table 200 of FIG. 2 illustrates a simplified version of the possible conditions for one component within each of the four categories.

Referring to FIG. 2, the table 200 includes a category field 201, a reference component field 202, and the pre-defined options field 203. Table 200 also includes a number of options field 204. The category field 201 in one embodiment includes the categories for which reference dentition condition information is stored. In the exemplary embodiment, the categories may include: sagittal, vertical, horizontal, and arch length. In this exemplary embodiment, the reference component field 202 includes one common component within each dimension by which malocclusion is judged. The common pre-defined options field 203 includes the various levels of malocclusion for that dimension of the category. For example, the common malocclusions for the right canine component of the sagittal category are: Full class 2+(greater than full cusp Class 2), Full (Cusp) Class 2, Partial Class 2

(also called end-on Class 2), and so on. Within each dimensional component selection is also a selection for "normal."

Referring to FIG. 2, the number of options field 204 in one embodiment includes the number of possible reference conditions in each category, and also a total number of possible combinations of reference conditions. For example, the sagittal category has seven (7) possible reference conditions for the canine relationship component and the vertical category has seven (7) reference conditions for the anterior overbite component. The example shown yields 7×7×7'7=2401 possible combinations of reference conditions for the four components, as shown in the table 200 of FIG. 2. In one embodiment, each of these 2401 patient case combinations is stored in a database in storage unit 107 (FIG. 1), for example, by the central server 109 (FIG. 1). Since there can be numerous components used to describe each of the four main orthodontic dimensions and not just one component per dimension as illustrated, in practice, the total number of combinations that can be used to describe a patient may be substantially higher, but at the same time, will be a finite number such that it may be indexed, catalogued, and queried as described in FIG. 1.

In reference to the index table 200 illustrated in FIG. 2, an identifier may be composed of a four-position, or "four-bit" matrix: ABCD. In this four-bit matrix, in one embodiment of the present invention, the "A" position in the matrix corresponds to the sagittal dimension, the "B" position in the matrix corresponds to the vertical dimension, the "C" position in the matrix corresponds to the horizontal dimension, the "D" position in the matrix corresponds to the arch length dimension.

The actual number or letter in the position of each "bit" of the matrix may be associated with the corresponding condition within the category. For example, referring again to the exemplary table 200 of FIG. 2, an identifier of 3256 represents: a right canine partial Class 2, with moderate anterior deep bite, upper midline to the left 0-1 mm, and lower moderate crowding. This "3256" identifier corresponds to an address in an indexing database stored in storage unit 107 which has stored in the database, related clinical information for the particular pairing of "3256" to a user-defined treatment goal (for example, discussed in further detail below with reference to FIG. 4).

Dental Characterization Database

Referring back to FIG. 1, the indexing system 100 in one embodiment of the present invention may also be used to represent one or more teeth within a patient's dentition. Typically an adult patient's dentition includes 32 teeth. Dentists usually characterize five surfaces of each tooth: mesial, occlusal/incisal, distal, buccal/facial, and lingual. Each of these surfaces may be natural or covered by a restoration such as silver amalgam, composite, porcelain, gold, or metal crown. The tooth may also be missing or have been treated with a root canal or an implant. These combinations may be represented with an indexing system for the initial dentition, target dentition (treatment goal), and final dentition which is the outcome of the treatment.

For each tooth in a patient's dentition, there may be a number of possible conditions based on the characteristics of the tooth, such as the surface of the tooth and whether the tooth as been treated or is missing. The combinations of different possible conditions of the teeth define a matrix. An exemplary embodiment of the present invention includes a 32-position address within the matrix, where each position in the address corresponds to a tooth in a patient's dentition and includes a sub-address in which alphanumeric characters or other representations represent the current condition of the tooth.

A "5-bit" sub-address for each tooth includes positions 12345 where each of the positions "1" to "5" represents one of the five surfaces of the tooth. In particular, position 1 of the sub-address corresponds to the mesial surface of the tooth, position 2 of the sub-address corresponds to the occlusal or incisal surface of the tooth, position 3 of the sub-address corresponds to the distal surface of the tooth, position 4 of the sub-address corresponds to buccal or facial surface of the tooth, and position 5 of the sub-address corresponds to the lingual surface of the tooth.

Moreover, each of the following characters "A" to "N" corresponds to a condition of the particular surface of the tooth in the sub-address.

A = amalgam
B = composite
C = porcelain veneer
D = gold
E = porcelain crown
F = gold crown
G = gold crown with root canal
H = porcelain crown with root canal
I = amalgam with root canal
J = composite with root canal
K = gold crown with implant
L = porcelain crown with implant
M = missing
N = natural For example, consider the following patient identifier 1:NNABN. The identifier 1:NNABN would represent: tooth number 1 of a 32-bit address which has a natural mesial surface (subaddress position 1), an occlusal amalgam (sub-address position 2), a natural distal surface (subaddress position 3), a buccal/facial composite (subaddress position 4), and a natural lingual surface (subaddress position 5).

In an exemplary embodiment of patient's initial dentition, target dentition (treatment goal), and final dentition, such example may be configured as:

TotalAddress=SubAddress1:SubAddress2:SubAddress3
SubAddress1=Teeth 1-32 initial
SubAddress2=Teeth 1-32 target
SubAddress3=Teeth 1-32 current, timepoint today whereby each of the of the 1-32 may further include an addition sub-matrix of 1-5 surfaces as previously described.

In this manner, dentists may easily query their practice database to determine how much dental work has been done and remains to be done. They can also track trends of use in their practice and what are the most common procedures in the practice. The patient matrix may also be used in forensics for patient identification purposes, as well as for national security and other security purposes.

FIG. 3 illustrates an exemplary tabulation of the possible treatment goals of the indexing system treatment goal matrix stored in the storage unit 107 of FIG. 1 in accordance with one embodiment of the present invention. Four examples of treatment goals are the following:

Treatment Goal 1: Align for restorative dentistry—the objective of this goal is to better position specific teeth for the purpose of improved placement of dental restorations such as crowns, bridges, and implants. Some of the patient's dental components may be left as is (untreated) if they do not contribute to the purpose of improvement of the restorative goal.

Treatment Goal 2: Esthetic alignment—the objective of this goal is to align the patient's anterior teeth for the purpose of improved esthetics. Generally speaking, the patient's bite may be left as is (untreated) if it does not contribute to the purpose of improving the esthetic component of the patient's smile.

Treatment Goal 3: Align to Class 1 canine function—the objective of this goal is to improve the anterior function of the teeth while also improving the anterior esthetic component. Generally speaking, the patient's posterior occlusion may be left as is if it does not contribute to the improvement of the canine function and/or anterior esthetics.

Treatment Goal 4: Align to ideal—the objective of this goal is to make the entire bite to "textbook" ideal, including both the canine and molar function.

Figures 4, 5:
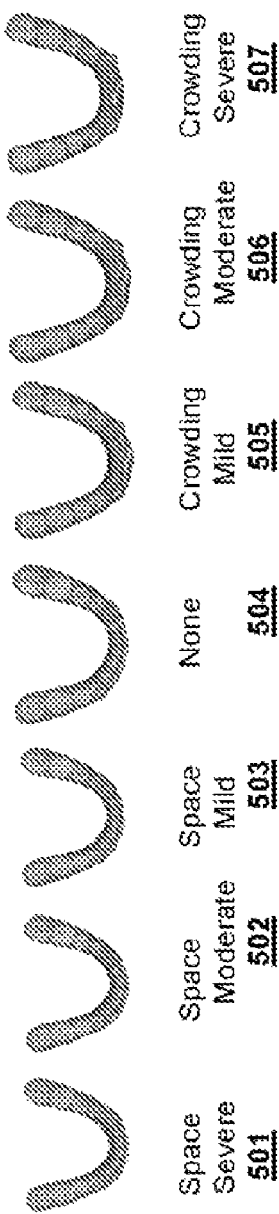
FIG. 4 illustrates a matrix representation for the possible treatment goals shown in FIG. 3 formatted in accordance with the tabular representation shown in FIG. 2 in accordance with one embodiment of the present invention.
FIG. 5 illustrates the lower arch length category for use in the indexing system in accordance with one embodiment of the present invention.

FIG. 4 illustrates an expanded version of FIG. 3 using the characteristics as defined by the tabulation shown in FIG. 2. More specifically, each of the four treatment goals identified in FIG. 3 may be further refined and formatted according to the tabulation and indexing shown in FIG. 2 to describe the target objective of treatment in greater detail according to each individual component.

For example, for the treatment goal 1 for alignment for restorative dentistry, an example of this goal according to the 4-bit matrix format in FIG. 2 may be XXX4 where the "X" is the patient's existing relationship for that component left untreated, and only the fourth digit is planned for treatment. Furthermore, for the treatment goal 2 for esthetic alignment, an example of this goal according to the 4-bit matrix format in FIG. 2 may be XX44 where "X" is the patient's existing relationship for that component left untreated, and only the third and fourth digits (representing the transverse and arch length components, respectively) are planned for treatment.

In addition, for treatment goal 3 for alignment to Class 1 canine, an example of this goal according to the 4-bit matrix format in FIG. 2 may be 4X44 whereby "X" is the patient's existing relationship for that component left untreated. In this example, only the second digit component (corresponding to the vertical dimension) is not planned for treatment. Finally, for treatment goal 3 for alignment to ideal, an example of this goal according to the 4-bit matrix defined in FIG. 2, may be 4444.

There are various ways to generate an identifier which represents a patient's unique problem or case type. Traditionally, the method has been to describe and define a characteristic and have the trained individual subjectively identify the condition or "label" which best represents the patient's condition. To reduce the variability in this method requires calibration and/or objective measures to define each of the labels.

Another method involves using a visual image-based interface. To characterize a patient's dentition, a user compares the patient's dentition to images of reference dentition conditions which depict the severity of malocclusion, or lack thereof. The user then identifies where the patient's dentition condition falls within a range of reference conditions depicting malocclusion and selects the image that either best represents the patient, or selects a relative position of the patient's condition from a continuous gradient of patient image depictions of the specific problem. The visual image interface can be presented to the user without any descriptions or labels to avoid any pre-conceived biases associated with the label.

Visual images have been previously described in the ICON indexing system for example, to describe an esthetic component of the patient. In the ICON system, the assessor selects 1 of 10 images which best represents the patient's anterior esthetic component. Through calibration, multiple users are then able to determine a patient's esthetic component with reasonable consistency. The use of a visual interface to capture every component of the patient's orthodontic dental condition however, has not previously been described as an interface for creation of a digital patient database.

FIG. 5 illustrates the lower arch length component 500 for use in the indexing system in accordance with one embodiment of the present invention. This illustration of the lower arch length component 500 is an exemplary visual scale allowing the user to select an image which is similar to the patient's dentition condition. Referring to FIG. 5, there are shown seven images of the lower arch, each representing a possible reference condition for the lower arch length category. In this exemplary embodiment, images 501-507 represents the 7 images corresponding to the individual fields for the "Lower Arch Length" component of "Arch Length" dimension of FIG 2. The user simply selects which of the seven images is best represented in the patient. Or they may be able to select where in between two adjacent images the patient can be best described. They do not need to know what the technical label or term is; they simply need to select an image or area between two images based on direct comparison of the existing condition to the pictures presented.

In the exemplary embodiment shown in FIG. 5, each of the seven images 501-507 has a corresponding predefined alphanumeric character. Thus, when an image is selected, the associated predefined alphanumeric character is added to the identifier address of the patient. By labeling each category with an alphanumeric character, the patient's dentition may be characterized through alphanumeric addressing. The output to the user may explain the specific details of their selection in greater detail, including the technical description and treatment options associated with such a condition. In an alternate embodiment, an alphanumeric character may be generated when the user selects the area in between adjacent images, representing that the patient's condition falls in between the condition of the adjacent images selected. The user interface may also be a combination of both direct selection of the image as well as in-between selection of images.

Referring now to FIG. 6, an exemplary doctor and patient information display 600 for the indexing system 100 is illustrated in accordance with one embodiment of the present invention. This display 600 includes information input by a user into fields 601-603 to identify a patient. In particular, a patient's name is input into field 601, a patient's gender is input into field 602, and a patient's primary concern(s) is input into field 603. The preferred embodiment of field 603 is a check-box selection of pre-defined possible conditions which can then be catalogued according to the selections of the user. It will be appreciated that other patient information may be added. Once the patient information has been entered, a user can select a predefined input command or button to move onto the next display, which is illustrated in FIG. 7.

Figure 7:
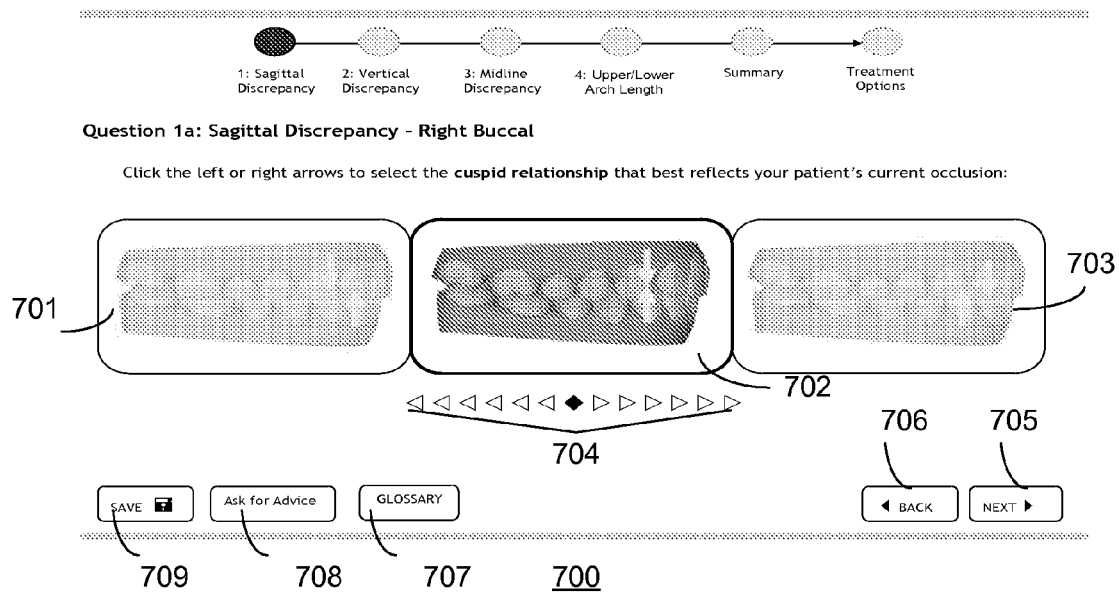
FIG. 7 illustrates an exemplary selection process display 700 for capturing one component of the sagittal dimension discrepancy for the patient's right side in one embodiment of the present invention.

Referring to FIG. 7, an exemplary selection process display 700 is shown for the sagittal dimension (matrix address position "A" in FIG. 2)—right buccal, right canine/cuspid component. A series of images of reference dentition conditions 701-703 are displayed in conjunction with buttons 704 allowing the images to be scrolled to the left or right. A user clicks the left or right arrow buttons 704 to select the image of the reference dentition condition that best reflects the patient's current condition specifically at the location(s) indicated by the focusing arrows indicated in 702. In this exemplary embodiment, a user clicks the left or right arrow buttons to select the cuspid (canine) relationship that is similar to a patient's current occlusion.

Once the selection is made, the next button 705 is pressed to move onto the next screen. The exemplary selection process display 700 also includes buttons 706-709 to allow a user to go back, access a glossary, ask for advice, and save the information, respectively.

Figure 8:
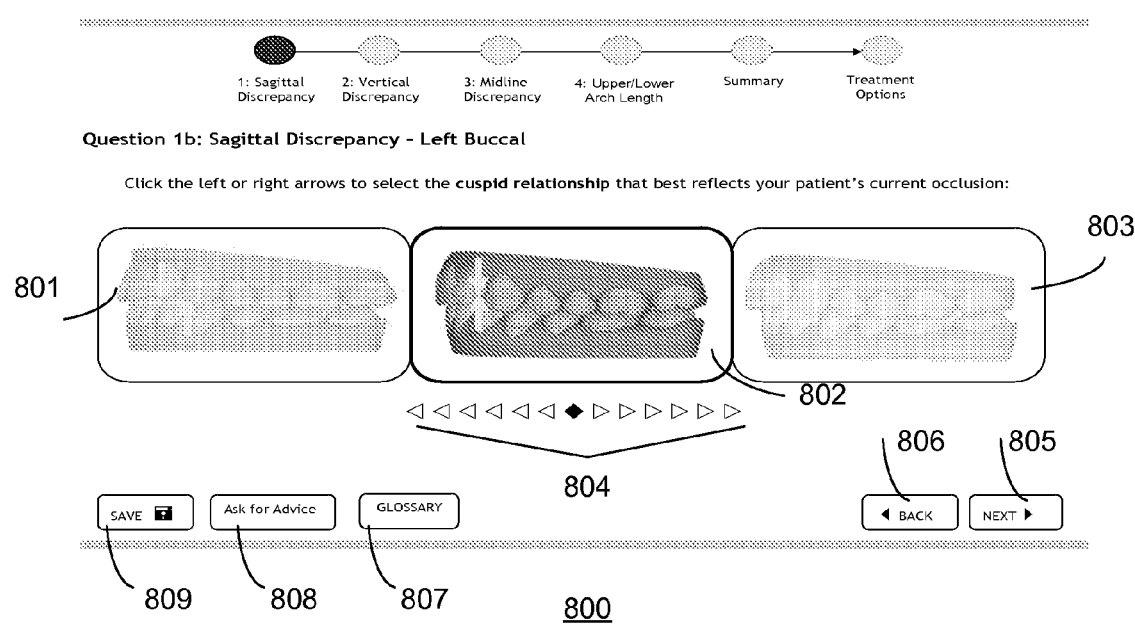
FIG. 8 illustrates an exemplary selection process display 700 for capturing one component of the sagittal dimension discrepancy for the patient's left side in one embodiment of the present invention.

Referring to FIG. 8, an exemplary selection process display 800 is shown for the sagittal category—left buccal, left cuspid component. A series of images of reference dentition conditions 801-803 are displayed in association with buttons 804 allowing the images to be scrolled to the left or right. A user clicks the left or right arrow buttons 804 to select the image of the reference dentition condition that best reflects the patient's current condition. In this exemplary embodiment, a user clicks the left or right arrow buttons to select the cuspid relationship that is similar to a patient's current occlusion.

Figure 9:
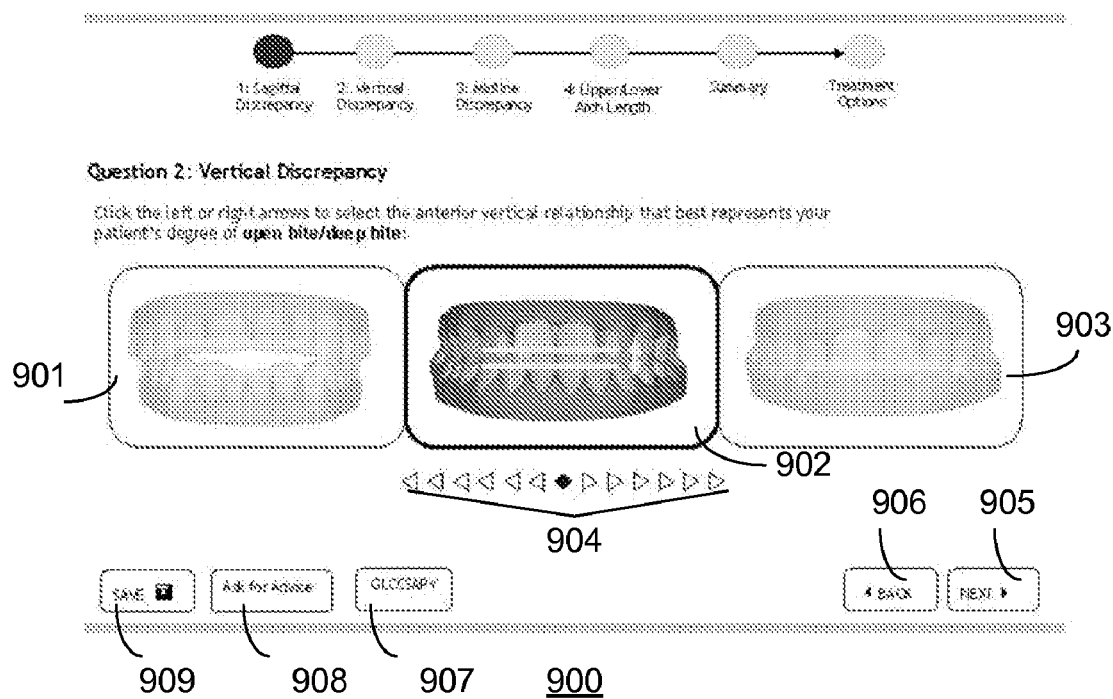
FIG. 9 illustrates an exemplary selection process display 900 for capturing one component of the vertical dimension in one embodiment of the present invention.

Once the selection is made, the next button 805 is pressed to move onto the next display which is illustrated in FIG. 9. The exemplary selection process display 800 also includes buttons 806-809 to allow a user to go back, access a glossary, ask for advice, and save the information, respectively.

Referring to FIG. 9, an exemplary selection process display 900 is shown for the vertical dimension (matrix address position "B" in FIG. 2)—anterior overbite component. A series of images of reference conditions 901-903 are displayed in conjunction with buttons 904 allowing the images to be scrolled to the left or right. A user clicks the left or right arrow buttons 904 to select the image of the reference dentition condition that best reflects the patient's current condition. In this exemplary embodiment, a user clicks the left or right arrow buttons 904 to select the anterior vertical overbite relationship component that is similar to a patient's degree of open or deep bite.

Figure 10:
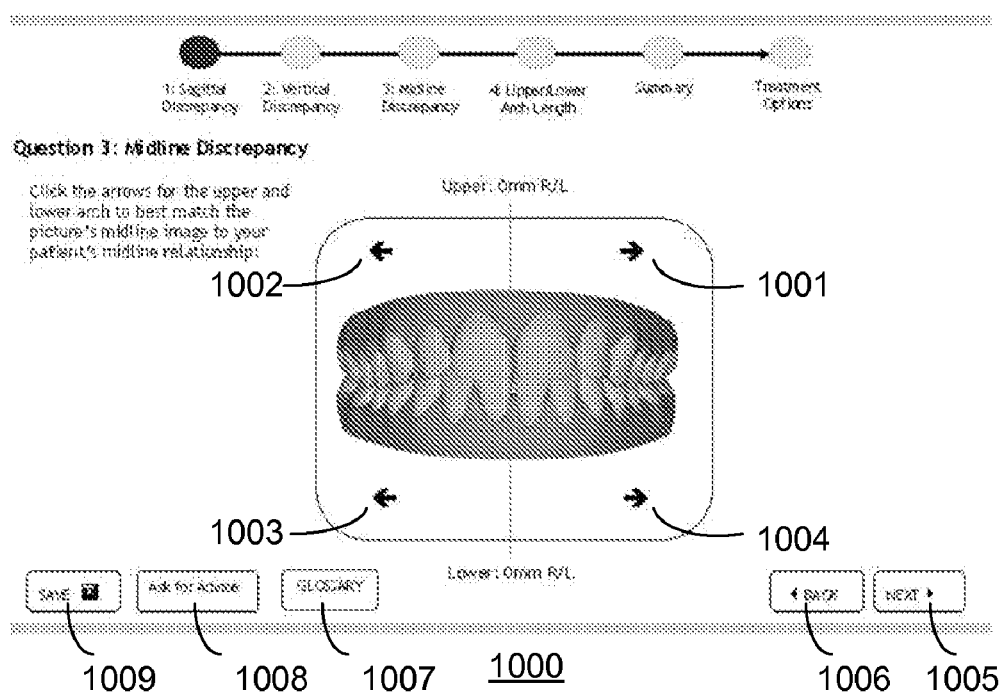
FIG. 10 illustrates an exemplary selection process display 1000 for capturing one component of the horizontal/transverse dimension in one embodiment of the present invention.

Once the selection is made, the next button 905 is pressed to move onto the next display, which is illustrated in FIG. 10. The exemplary selection process display 900 also includes buttons 906-909 to allow a user to go back, access a glossary, ask for advice, and save the information, respectively.

Figure 11:
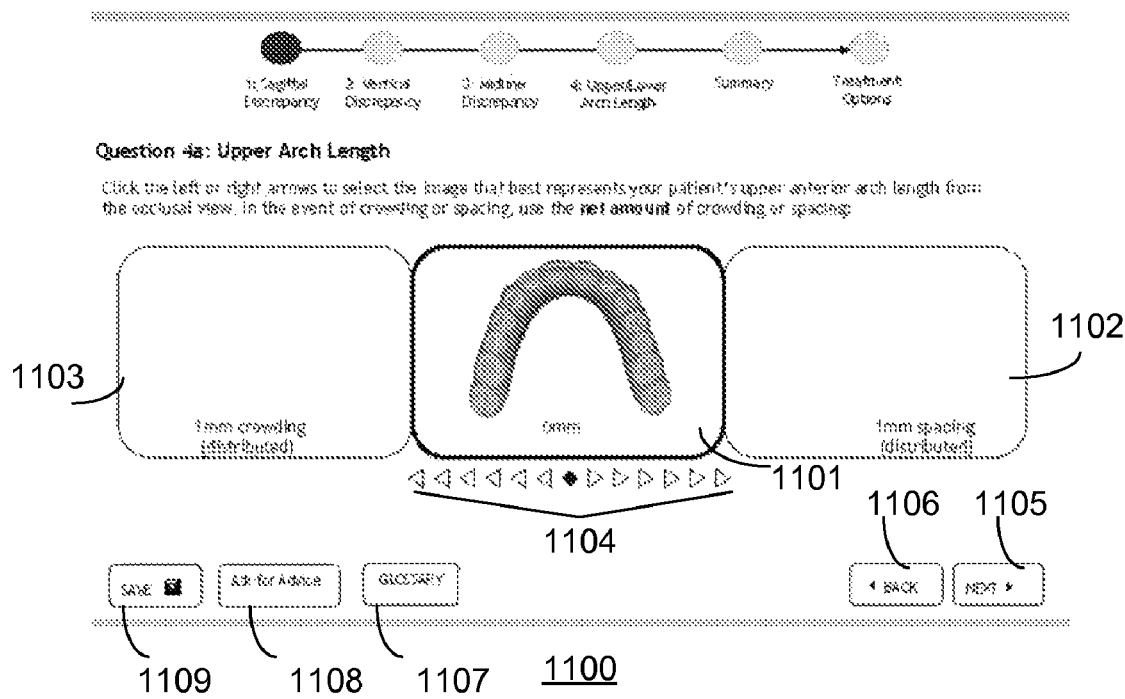
FIG. 11, an exemplary selection process display 1100 for capturing one component of the arch length discrepancy category in accordance with one embodiment of the present invention.

Referring to FIG. 10, an exemplary selection process display 1000 is shown for the horizontal/transverse dimension (matrix address position "C" in FIG. 2)—upper and lower midline components. An image 1010 representing a reference dentition condition is altered by clicking the upper arrows 1001-1002 corresponding to the upper arch of the image 1010, and by clicking the lower arrows 1003-1004 corresponding to the lower arch of the image 1010 to best match the midline of the image 1010 to a patient's midline component relationship. Once the selection is made, the next button 1005 is pressed to move onto the next display, which is illustrated in FIG. 11. The exemplary selection process display 1000 of FIG. 10 also includes buttons 1006-1009 to allow a user to go back, access a glossary, ask for advice, and save the information, respectively.

Referring to FIG. 11, an exemplary selection process display 1100 is shown for the upper arch length category. An image of a reference dentition condition 1101 and descriptions of reference dentition conditions 1102, 1103 are displayed in association with buttons 1104 allowing the reference dentition condition image and descriptions to be scrolled to the left or right. A user clicks the left or right arrow buttons 1104 to select the image or description of the reference dentition condition that best reflects the patient's current condition. In this exemplary embodiment, a user clicks the left or right arrow buttons 1104 to select the image or description of the reference dentition condition that is similar to a patient's upper arch length from the occlusal view. In this particular embodiment, if there is both crowding and spacing present, a user is instructed to use the net amount of crowding or spacing, but it may be possible to have each aspect captured independently.

Figure 12:
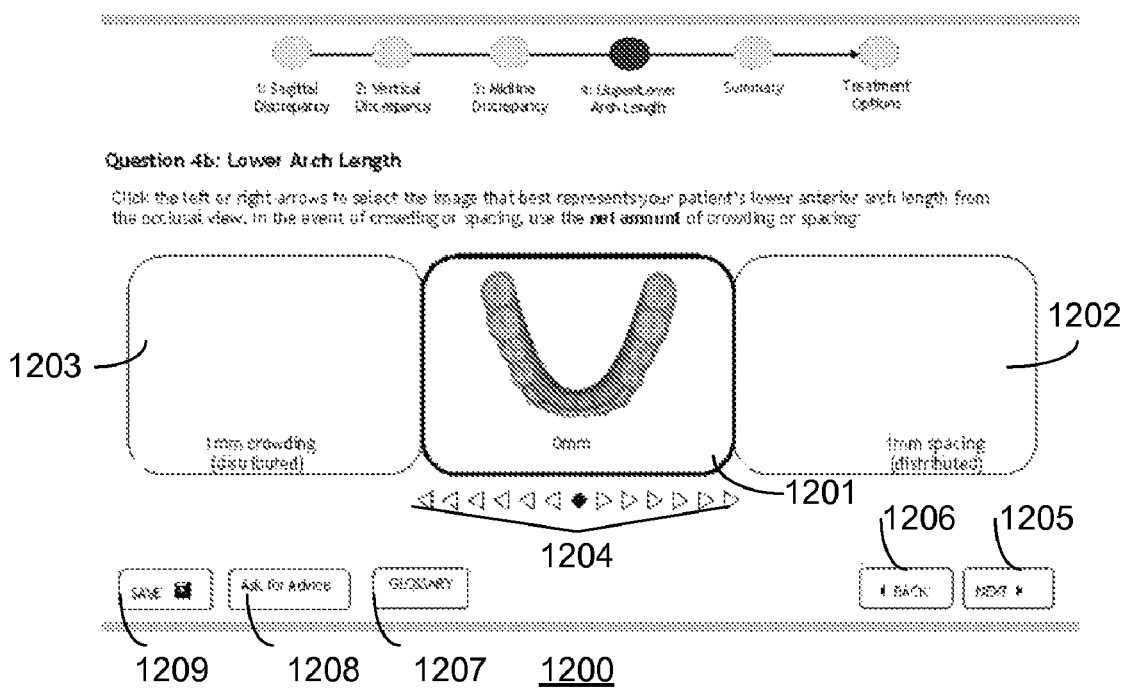
FIG. 12 illustrates an exemplary selection process display 1200 for capturing another component of the arch length discrepancy category in accordance with one embodiment of the present invention.

Again, once the selection is made, the next button 1105 is pressed to move onto the next display which is illustrated in FIG. 12. The exemplary selection process display 1100 also includes buttons 1106-1109 to allow a user to go back, access a glossary, ask for advice, and save the information, respectively.

Referring to FIG. 12, an exemplary selection process display 1200 is shown for the arch length dimension (matrix position "D" in FIG. 2)—lower arch length component. An image of a reference dentition condition 1201 and descriptions of reference dentition conditions 1202, 1203 are displayed in association with buttons 1204 allowing the reference dentition condition image and descriptions to be scrolled to the left or right. A user clicks the left or right arrow buttons 1204 to select the image or description of the reference dentition condition that best reflects the patient's current condition for the lower arch length component of arch length In this exemplary embodiment, a user clicks the left or right arrow buttons 1204 to select the image or description of the reference dentition condition that is similar to a patient's lower arch length from the occlusal view. In this example, if both crowding and spacing are present, the user is instructed to use the net amount of crowding or spacing. It may be possible however to capture crowding and spacing independently in order to derive the net discrepancy.

Once the selection is made, the next button 1205 is pressed to move onto the next display, which is illustrated in FIG. 13. The exemplary selection process display 1200 of FIG. 12 also includes buttons 1206-1209 to allow a user to go back, access a glossary, ask for advice, and save the information, respectively.

FIG. 13 illustrates an exemplary patient summary tabulation 1300 for output display on terminal 101 for use in the indexing system in accordance with one embodiment of the present invention. The exemplary patient summary display 1300 is generated from the information input from previous displays 600-1200, as illustrated in corresponding FIGS. 6-12, respectively. Referring to FIG. 13, the selections made during the processes and displays described above and illustrated in conjunction with FIGS. 6-12 are summarized as shown in the summary display 1300 in one embodiment of the present invention.

For example, for each reference dentition category including sagittal, vertical, horizontal and arch length, the corresponding malocclusion reference component (for example, right canine, anterior overbite, upper midline relative to lower midline, and lower arch length, respectively), and each of which is associated with a selected one of the pre-defined options (for example, right canine partial Class 2, moderate anterior deep bite, upper midline to left 0-1 m, and lower moderate crowding, respectively). Also can be seen from FIG. 13 is the selected value of the selected pre-defined options 203 (FIG. 2) as tabulated and illustrated in FIG. 2. The user is also able to edit the dentition condition information in each of the categories by selecting the corresponding "EDIT" button to go back to the page desired and reselecting the image corresponding to that category.

In this manner, in one embodiment of the present invention, the information input by the user during the selection process is indexed and catalogued in a patient database (for example, the database 1400 shown in FIG. 14 below) of the indexing system 100. In one embodiment of the present invention, the selection process discussed in conjunction with FIGS. 6-12 for the indexing and cataloguing is transparent to the user. The patient information input by the user in the selection process is used to generate both the summary display as illustrated in FIG. 13 and an identifier representing the dentition conditions of the patient. FIGS. 6-12 illustrate the selection process display 600 for use in the indexing system 100 for various categories in accordance with one embodiment of the present invention. This is the selection process for inputting a patient's dentition information. It will be appreciated that although FIGS. 7-12 illustrate reference dentition conditions represented by pictorial images, the present invention is not intended to be limited to such representations. The reference dentition conditions may also be represented by symbols, icons, descriptions, graphs, 3-D objects, radiographs, forms, and other types of images. The reference conditions may also be user-defined through an interactive graphical image such that the user best recreates the condition observed in the patient as a means of input for the system.

FIG. 14 illustrates a patient database 1400 for use in the indexing system 100 in accordance with one embodiment of the present invention. The patient database 1400 includes a patient field 1401, an indexing database address field 1402, and one or more category fields 1403. In the exemplary database of FIG. 14, the category fields 1403 include a sagittal category field 1404, a vertical category field 1405, a horizontal category field 1406, an upper arch length category field 1407, a lower length category field 1408, a rotation field 1409, a vertical correction field 1410, and a midline correction field 1411.

Referring to FIG. 14, the patient field 1401 includes the patient name. The indexing database address field 1402 includes the patient identifier. This patient identifier corresponds to an address in the indexing database 300, for example, as shown in FIG. 3. The address in the indexing database 300 is associated with treatment information for that particular diagnostic combination. The category fields 1403, which in this exemplary embodiment are the sagittal category field 1404, the vertical category field 1405, the horizontal category field 1406, the upper arch length category field 1407, the lower length category field 1408, the rotation field 1409, the vertical correct field 1410, and the midline correct field 1411, include the patient's one or more dentition conditions in the respective categories. For example, referring to FIG. 14, patient L. Smith's dentition condition in the sagittal category field 1404 is class I. Patient M. Jones' dentition condition in the upper arch length category field 1407 is normal spacing. The category fields also indicate whether the particular reference condition is eligible for treatment.

In this manner, the patient identifier may be configured to represent the patient conditions. For example, referring to the indexing database address field 1402, it is shown that L. Smith's identifier is 55772752. Since the identifier includes eight positions, the identifier is an eight-position matrix. The number in each position of the identifier represents a particular condition within a particular category. In this exemplary embodiment, the first position of the identifier matrix represents the patient condition in the sagittal category. For example, the sagittal category field 1404 indicates that L. Smith has a class I malocclusion. Thus, the number 5 in the first position of the identifier represents a class I malocclusion in the sagittal category.

Referring back to FIG. 14, the second position of the identifier matrix represents the patient condition in the vertical category. For example, the vertical category field 1405 indicates that L. Smith has normal occlusion. Thus, the number 5 in the second position of the identifier represents a normal occlusion in the vertical category. The third position of the identifier matrix represents the patient condition in the horizontal category. For example, the horizontal category field 1406 indicates that L. Smith has a cross bite. Thus, the number 7 in the third position of the identifier represents cross bite in the horizontal category.

Moreover, the fourth position of the identifier matrix represents the patient condition in the upper arch length category. For example, the upper arch length category field 1407 indicates that L. Smith has moderate crowding. Thus, the number 7 in the fourth position of the identifier represents moderate crowding in the upper arch length category. In addition, the fifth position of the identifier matrix represents the patient condition in the lower arch length category. For example, the lower arch length category field 1408 indicates that L. Smith has moderate spacing. Thus, the number 2 in the fifth position of the identifier represents moderate spacing in the lower arch length category.

In addition, the sixth position of the identifier matrix represents the patient condition in the rotation category. For example, the rotation category field 1409 indicates that L. Smith has <20° rotation. Thus, the number 7 in the sixth position of the identifier represents <20° rotation in the rotation category. Further, the seventh position of the identifier matrix represents the patient condition in the vertical correct category. For example, the vertical correct category field 1410 indicates that L. Smith has no intrusion/extraction. Thus, the number 5 in the seventh position of the identifier represents no intrusion/extraction in the vertical correct category.

Finally, referring yet again to FIG. 14, the eighth position of the identifier matrix represents the patient condition in the midline correct category. For example, the midline correct category field 1411 indicates that L. Smith has >2 MM midline correct. Thus, the number 2 in the eighth position of the identifier represents >2 MM midline correct in the midline correct category.

In addition, in one embodiment of the present invention, the conditions in the categories are arranged in ascending order by difficulty and the categories are sorted in order of difficulty so that it is possible to define a matrix where 11111 is the mildest case and 33233 is the most severe case. Additionally, each index in the matrix is weighted to derive a composite score of the overall case.

FIG. 15 illustrates an alternate embodiment of the present invention for capturing an address in the selection process for use in the indexing system. FIG. 15 illustrates the table 200 of FIG. 2 used directly as a graphical interface. In such embodiment, each reference condition as shown and illustrated in tabular format as rectangles may be represented as user input buttons with text which may be clicked to highlight and select the appropriate reference condition. The assumption for this type of interface is that the user understands the definitions of the text in order to select the appropriate button. When the buttons are pressed to select a particular reference condition, the selections are highlighted (shown in bold in FIG. 15). Clicking any button twice will deselect the initial selection so that another selection can be made. In this manner, users who are more familiar with the various types of reference conditions may be able to input the information more quickly than through a visual-image based interface. In this example, the generated address would be "3256." The "Selected Value" column on the right side of FIG. 15 is in in one embodiment, transparent to the user/patient, and not displayed to the user since the address has no relevance to the end user, and is important only for the database query.

FIG. 16 illustrates an exemplary series of database addresses generated by combining the initial condition address with the treatment goal address in one embodiment of the present invention. As indicated from the exemplary table 200 of FIG. 2, there are 2,701 possible patient case combinations or addresses for four components of seven possible selection options each. Thus, an identifier address points to one of the 2,701 possible combinations in the database. Each identifier is associated with a field stored in a database of the storage unit 107 (FIG. 1). An identifier may be extended so that it represents the patient's condition at different time points. For example, the database may be structured such that time points for initial dentition, target dentition, and actual final dentition are captured as separate addresses. For example, consider the following address:

ABCD: A'B'C'D':A"B"C"D"

In this arrangement, the first four positions "A" to "D" of the matrix represent the patient's initial dentition (as previously described), positions "A'" to "D'" of the matrix represent the patient's target dentition or treatment goal, and positions "A''" to "D''" of the matrix represent the patient's actual final dentition or treatment outcome. Because the number of positions in the matrix may be variable, and since each position can include symbols, alphanumeric characters or other representations, the depth of individual patient cases that is stored is may be detailed and specific to the patient and/or the associated profile or condition. Using the 4 possible treatment outcomes illustrated in FIG. 4 and the 2,701 possible combinations in FIG. 2, this equates to 2,701×4=10,804 possible paired combinations between initial and goal.

FIG. 17 illustrates an exemplary database for a patient with an index address of "3256" and the four possible treatment goals of 1 through 4. The resulting four combined addresses have different data for each of the parameters. This information is reported to the user either (1) upon completion of the case characterization, whereby all possible treatment goal options are presented to the user or (2) upon completion of the case characterization and selection of a single treatment goal, whereby only the information from this address-goal pair is presented to the user.

For each of these paired combinations, a combined address can be created, with database assets in a "digital mailbox" associated with each address. Assets for each digital mailbox can include, but is not limited to: treatment plan information related to the case-treatment goal pairing, such as a text description of the treatment condition and goals, treatment precautions, treatment length estimates, doctor skill set requirements, prescription data, sample case data, and case difficulty. This data may be generated using expert opinion, computational algorithms, and/or historical case content.

For example, with respect to FIG. 13, where the case is identified as a "3256" and using the 4 types of treatment goals as shown in FIG. 4, combining the two yields four distinct database addresses: 3256:1, 3256:2, 3256:3, and 3256:4. Each of the addresses can be populated with information specific to the case-treatment goal combination. All four options can be simultaneously displayed to the user as "treatment options" or the user can select a specific treatment goal and have a single specific resulting treatment option data displayed. It is also conceivable that the user may also select any number of specific goals, and each of the data associated with each goal selected is reported to the user depending on the initial condition parameters selected.

Figure 18:
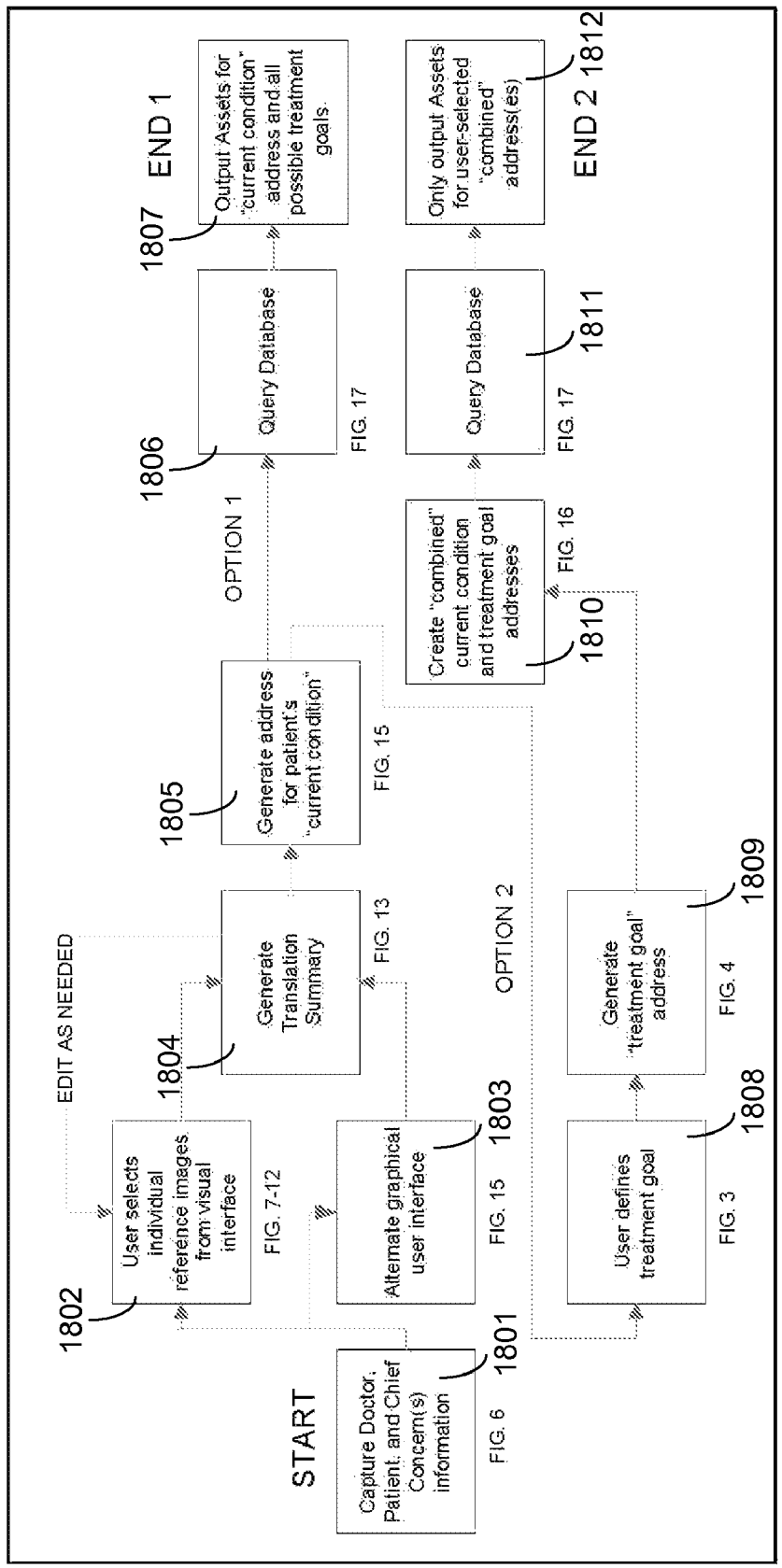
FIG. 18 is a flowchart illustrating the procedure for identifying a dentition profile using the indexing system in accordance with one embodiment of the present invention.

FIG. 18 illustrates a process 1800 for identifying a dentition problem or condition of a patient. The process 1800 is discussed more fully in conjunction with FIGS. 6-17. At step 1801, the user starts by entering identification information such as doctor and patient name, in addition to patient chief concern(s) (FIG. 6). In one embodiment, this comparison may be performed by the central server 109 (FIG. 1) based on information received, for example, from the terminal 101, and/or based on stored information retrieved from the data storage unit 107. This and other related transactions in the process may be performed over a data network such as the internet via a secure connection. The user then selects one of two user interfaces to input the patient's dental condition. The preferred method for the novice user is the visual-user interface (FIG. 7-12) shown as step 1802. The advanced user will likely prefer the alternative user interface (FIG. 15) illustrated as step 1803.

Referring to FIG. 18, at step 1804 an initial dentition condition of a patient in each category is compared to one or more reference conditions in the same category. After comparing the initial dentition condition of the patient in each category to one or more reference conditions for each respective category, at step 1804, the selected reference condition similar to the initial patient condition in the same category is received. Thereafter, at step 1805, the patient identifier is then generated based on the combination of alphanumeric characters corresponding to the selected reference conditions. Edits can be made to the inputs during the summary page review (step 1804) until the user is satisfied with the information submitted.

The output following the completion of the data input is a translation summary (FIG. 13), which formats the user input into technically relevant and correct terminology. At the same time, the user input is also translated into a database address representing the current patient condition (FIG. 15)—step 1805. Once the database address is created, the user can choose to view all possible treatment options for this patient (OPTION 1), or specifically select a treatment goal and view the specific goal associated with the user's selection (OPTION 2). To view all the possible treatment options for the patient (OPTION 1), the database (FIG. 17) is queried at step 1806, and all data associated with the input address is presented to the user at step 1807 (END 1).

Referring back to FIG. 18, if the user desires to select a specific goal, the specific goal is first defined by the user through a selection interface at step 1808 (FIG. 3), and the selection is then translated into a database address at step 1809 (FIG. 4), and the two addresses (patient condition and treatment goal) merged to create a combined address or index at step 1810 (FIG. 16). This combined address is then used to query the database ate step 1811 (FIG. 17) in order to produce data specific to a single patient condition-treatment goal combination at step 1812 (END 2).

For OPTION 2, it may also be possible that the user can select multiple goals and only the data specific to those selected goals be produced for the user. Once the user has reached END 1 or END 2, the user has the option to purchase the product for the purpose of any one of the selected treatment goals, by selecting a pre-populated or semi-populated treatment prescription which can be part of the output data presented to the user through this experience.

As discussed above, the user interface can provide one or more patient cases from the indexing database that matches the patient problem. Additionally, a range of patient cases from the indexing database that address specific components of the patient's problem can be provided. In this manner, in one embodiment of the present invention, search tools may be created to run statistics using the patient identifiers. For example, one search request may be to find all 131X cases. In this exemplary search request, X represents any character in the fourth position of the address. Thus, the search request would be to find all patient identifiers having "131" as the first 3 digits of their patient identifier address.

By labeling historically treated cases with this identification methodology, a catalog of orthodontic treatment can be created for future reference when planning treatment and assessing treatment outcomes. The result is a front-end user interface for capturing the description of an orthodontic condition and classifying the orthodontic condition in a systematic scalable way. Referring again to FIG. 18, once the identifier is generated at step 1805, one or more treatment options can be determined using information generated from a database query. The generated one or more treatment options may be stored in the data storage unit 107 (FIG. 1), and also, be provided to the terminal 101 for display on the display unit.

Given the diagnosis and treatment planning of orthodontic treatments can include a significant subjective component that may vary depending upon the doctor's preferences and level of training, the indexing system provides a comprehensive, robust, and a substantially objective approach to establishing the patient diagnosis, treatment goal, and treatment plan. The patient identifier of the present invention which represents the patient's case, as well as the target treatment goal and final outcome enables treatment outcome profiles to be objectively catalogued, and for the catalog to be evaluated based on probabilities and distributions. Indices such as prognosis and case difficulty can be assigned to matrix combinations, enabling similar cases to be treated like similarly successful cases. Treatment options may be correlated for completeness and ease of use. Treatment products, such as appliances, may be associated with specific matrix combinations so that their suggested use is more closely tied to a successful outcome.

Within the scope of the present invention, other embodiments for inputting a patient's dentition condition are also contemplated. For example, a configurable three-dimensional model may be used to input the information. In such embodiment, the user may recreate the patient dentition condition for the dimension. Alternatively, a three-dimensional graphics model may be staged to represent the entire range of possible reference conditions for any given dimension. In such embodiment, a user manipulates a slider to match a stage of the range which is closest to the actual patient condition.

It will also be appreciated that this method of objectively characterizing a case according to individual components is not limited to the time points of pre-treatment, treatment goal, and post-treatment, and that any time point during treatment and following treatment may be also catalogued in a similar fashion using the same input and database system.

It will also be appreciated that in this exemplary embodiment although only one reference condition is discussed as being selected for a particular category, the present invention is not intended to be so limiting. The selection of one or more reference conditions within each category is within the scope of the present invention.

Accordingly, a method for characterizing a dentition of a patient in one embodiment of the present invention includes comparing an initial patient condition in each of a plurality of dentition categories with one or more reference conditions in each of the plurality of dentition categories, where each of the one or more reference conditions has a corresponding representation, selecting at least one reference condition in one or more of the plurality of dentition categories, where each selected reference condition is similar to the initial patient condition in a same dentition category, and generating a patient identifier based on the corresponding representations of each selected reference condition.

In one aspect, the plurality of dentition categories may include at least two of: sagittal, vertical, horizontal, upper and arch length dimensions, or a number of a tooth in a dentition of a patient.

Moreover, the method may further include determining whether each initial patient condition is indicated for treatment based on treatment information corresponding to the selected reference condition, providing one or more treatment options for each initial patient condition indicated for treatment, where the one or more treatment options include one or more of a treatment description, a treatment goal, a time to complete the treatment, a difficulty level, and a skill level to complete the treatment, an example of the treatment option.

Further, in another aspect, the method may also include comparing at least a portion of the patient identifier with one or more reference identifiers, wherein each of the one or more reference identifiers includes an initial reference dentition and a final reference dentition, selecting at least one reference identifier from the one or more reference identifiers, wherein the selected reference identifier includes the portion of the patient identifier, and determining a final patient dentition based on the final reference dentition corresponding to the selected reference identifier.

A method for characterizing a dentition of a patient in accordance with another embodiment of the present invention includes receiving an initial dentition of a patient, generating an initial profile representing the initial dentition of the patient, identifying an initial malocclusion from the initial profile, and comparing at least a portion of the initial profile with one or more reference profiles of reference dentitions, where said one or more reference profiles includes a reference malocclusion substantially similar to the initial malocclusion at the beginning, during any treatment stage, or final outcome treatment position.

Also, the method may also include the step of selecting at least one of the one or more reference profiles, where said one or more reference profiles has a related final reference dentition.

Additionally, in a further aspect, the method also include providing a target dentition of the patient based on the final reference dentition.

The step of generating an initial profile in one embodiment may include visually categorizing the initial dentition of the patient.

Moreover, the method may also include identifying one or more treatment options associated with the one or more reference profiles.

A system for providing an orthodontic profile indexing system in accordance with still another embodiment of the present invention includes a storage unit, and a controller unit operatively coupled to the storage unit, and configured to compare an initial patient condition in each of a plurality of dentition categories with one or more reference conditions in each of the plurality of dentition categories, where each of the one or more reference conditions has a corresponding representation, select at least one reference condition in one or more of the plurality of dentition categories, where each selected reference condition is similar to the initial patient condition in a same dentition category, and to generate a patient identifier based on the corresponding representations of each selected reference condition.

The controller unit may be configured to determine whether each initial patient condition is eligible for treatment based on treatment information corresponding to the selected reference condition, and to provide one or more treatment options for each initial patient condition eligible for treatment.

Also, the controller unit may be further configured to compare at least a portion of the patient identifier with one or more reference identifiers, where each of the one or more reference identifiers includes an initial reference dentition and a final reference dentition, to select at least one reference identifier from the one or more reference identifiers, where the selected reference identifier includes the portion of the patient identifier, and to determine a final patient dentition based on the final reference dentition corresponding to the selected reference identifier.

In addition, a terminal may be operatively coupled to the controller unit, and configured to transmit one or more of the initial patient condition, where the terminal may be further configured to include a display unit.

A system for characterizing a dentition of a patient in accordance with still another embodiment of the present invention includes a central controller unit configured to generate an initial profile representing the initial dentition of the patient, to identify an initial malocclusion from the initial profile, and to compare at least a portion of the initial profile with one or more reference profiles of reference dentitions, wherein said one or more reference profiles includes a reference malocclusion substantially similar to the initial malocclusion.

In another aspect, a user terminal may be operatively coupled to the central controller unit, the user terminal configured to transmit the initial dentition of the patient.

The central controller unit may be further configured to select at least one of the one or more reference profiles, wherein said one or more reference profiles has a related final reference dentition.

In addition, the central controller unit may be further configured to provide a target dentition of the patient based on the final reference dentition.

The central controller unit may be further configured to visually categorize the initial dentition of the patient.

Moreover, the central controller unit may be further configured to identify one or more treatment options associated with the one or more reference profiles.

In yet still a further aspect, a storage unit may be configured to store one or more of an initial profile an initial malocclusion, and a reference malocclusion.

The various processes described above including the processes performed by the central server 109 (FIG. 1) in the software application execution environment in the indexing system 100 including the processes and routines described in conjunction with the Figures may be embodied as computer programs developed using an object oriented language that allows the modeling of complex systems with modular objects to create abstractions that are representative of real world, physical objects and their interrelationships. The software required to carry out the inventive process, which may be stored in the memory or data storage unit 107 of the indexing system or internally (not shown) within the central server 109, may be developed by a person of ordinary skill in the art and may include one or more computer program products.

While the characterization of adult dentition has been discussed in conjunction with the embodiments described above, the various embodiments of the present invention may be used for the characterization of child dentitions. In addition, in accordance with the embodiments of the present invention, the various aspects of the present invention may be manually implemented by the user, for example, using printout documentation, visual graphics, and/or photographic images of the conditions and/or treatment options, and further, may include, within the scope of the present invention, manual computation or calculation of the results. In this manner, within the scope of the present invention, the various embodiments discussed above in the context of a computerized system for implementing the aspects of the present invention, may be implemented manually.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method for characterizing a dentition of a patient, comprising:
   accessing a database including one or more reference conditions in each of a plurality of dentition categories, each reference condition including a corresponding first value;
   determining, using a computer, a similar reference condition to an initial patient condition in each of the plurality of dentition categories by:
      comparing the initial patient condition in each of the plurality of dentition categories with the one or more reference conditions in each of the plurality of dentition categories; and
      selecting at least one reference condition in one or more of the plurality of dentition categories that is similar to the initial patient condition in a same dentition category; and
   generating, using the computer, a patient identifier matrix including a plurality of positions, wherein:
      each of the plurality of positions corresponds to one of the plurality of dentition categories; and
      each of the plurality of positions includes a second value equal to the first value of the selected reference condition for the corresponding one of the plurality of dentition categories.

2. The method of claim 1 wherein the plurality of dentition categories include at least two of: sagittal, vertical, horizontal, arch length, or a number of a tooth in a dentition of a patient.

3. The method of claim 2 wherein the plurality of categories are applied to at least two of: initial condition, treatment goal, final condition, during treatment condition, or post-treatment condition.

4. The method of claim 1 further including the step of defining a treatment goal wherein the treatment goal is not ideal in at least one dimensional component of sagittal, vertical, horizontal, or arch length.

5. The method of claim 1 further including the step of generating one or more of a treatment description, a time to complete the treatment, a difficulty level, or an example of the treatment option.

6. The method of claim 1 further comprising the step of:
   comparing at least a portion of the patient identifier with one or more reference identifiers, wherein each of the one or more reference identifiers includes an initial reference dentition and a final reference dentition;
   selecting at least one reference identifier from the one or more reference identifiers, wherein the selected reference identifier includes the portion of the patient identifier; and
   determining a final patient dentition based on the final reference dentition corresponding to the selected reference identifier.

7. The method of claim 6 further comprising the step of:
comparing at least a portion of the patient identifier and a treatment goal with one or more reference identifiers, wherein each of the one or more reference identifiers includes an initial reference dentition and a treatment goal reference identifier; and
determining a patient dentition goal based on the final reference dentition corresponding to the selected reference identifier.

8. A system for providing an orthodontic profile indexing system, comprising:
a non-transitory storage unit including one or more reference conditions in each of a plurality of dentition categories, each reference condition including a corresponding first value; and
a controller unit operatively coupled to the non-transitory storage unit, and configured to:
access the non-transitory storage unit; and
determine a similar reference condition to an initial patient condition in each of the plurality of dentition categories by:
comparing the initial patient condition in each of the plurality of dentition categories with the one or more reference conditions in each of the plurality of dentition categories,
selecting at least one reference condition in one or more of the plurality of dentition categories that is similar to the initial patient condition in a same dentition category, and
generating a patient identifier matrix including a plurality of positions, wherein:
each of the plurality of positions corresponds to one of the plurality of dentition categories; and
each of the plurality of positions includes a second value equal to the first value of the selected reference condition for the corresponding one of the plurality of dentition categories.

9. The system of claim 8 wherein the plurality of dentition categories include at least two of: sagittal, vertical, horizontal, arch length, or a number of a tooth in a dentition of a patient.

10. The system of claim 8, wherein the controller unit is configured to output one or more of a treatment description, a treatment goal, a time to complete the treatment, a difficulty level, or an example of the treatment option.

11. The system of claim 8 wherein the controller unit is further configured to compare at least a portion of the patient identifier with one or more reference identifiers, wherein each of the one or more reference identifiers includes an initial reference dentition and a final reference dentition, to select at least one reference identifier from the one or more reference identifiers, wherein the selected reference identifier includes the portion of the patient identifier, and to determine a final patient dentition based on the final reference dentition corresponding to the selected reference identifier.

12. The system of claim 8 further including a terminal operatively coupled to the controller unit, the terminal configured to transmit one or more of the initial patient condition.

13. The system of claim 12 wherein the terminal is further configured to include a display unit.

* * * * *